United States Patent [19]

Goof

[11] Patent Number: 4,992,048
[45] Date of Patent: Feb. 12, 1991

[54] TOOL FOR CLEANSING TOOTH ROOT CANALS

[76] Inventor: Sven K. L. Goof, 236A, Gl. Strandvej, DK-3050 Humlebaek, Denmark

[21] Appl. No.: 342,652

[22] Filed: Apr. 24, 1989

Related U.S. Application Data

[63] Continuation-in-part of Ser. No. 4,437, Dec. 9, 1986, abandoned.

[30] Foreign Application Priority Data

Apr. 15, 1985 [DK] Denmark .............................. 1686/85

[51] Int. Cl.⁵ .............................................. A61C 5/02
[52] U.S. Cl. ..................................... 433/102; 433/119
[58] Field of Search ............... 433/102, 127, 147, 119, 433/166, 116, 87

[56] References Cited

U.S. PATENT DOCUMENTS

| | | | |
|---|---|---|---|
| 736,101 | 8/1903 | Hough | 433/102 |
| 873,100 | 12/1907 | Skalstad | 433/102 |
| 1,015,039 | 1/1912 | Lasbury | 433/89 |
| 1,168,052 | 1/1916 | Bolls | 433/102 |
| 1,356,755 | 10/1920 | Bolls | 433/102 |
| 1,369,112 | 2/1921 | Jones | 433/102 |
| 4,229,168 | 10/1980 | Scholz | 433/102 |
| 4,353,696 | 10/1982 | Bridges | 433/119 |
| 4,364,730 | 12/1982 | Axelsson | 433/147 |
| 4,484,891 | 11/1984 | Nash | 433/116 |
| 4,492,574 | 1/1985 | Warrin et al. | 433/81 |
| 4,505,676 | 3/1985 | Gonser | 433/119 |
| 4,571,183 | 2/1986 | Nash | 433/116 |

FOREIGN PATENT DOCUMENTS

1242151  7/1986  U.S.S.R. .................. 433/102

*Primary Examiner*—John J. Wilson
*Attorney, Agent, or Firm*—Tilton, Fallon, Lungmus

[57] ABSTRACT

A broaching tool has a needle-shaped working portion (2) and a shank portion which is shaped for attachment in the distal end (18) of a drive bar (12) of a drive instrument for the tool. The shank portion of the tool has at least one bend (8) and preferably also a second oppositely directed bend (10). A proximal end (14) of the drive bar (12) of the drive instrument is adapted to be coupled to a vibratory element (16) which, thereby, is able to generate longitudinal high frequency vibrations in the drive bar (12). The distal drive bar end (18) is angled (B) about an axis (22) which acts as a hinge having a certain rigidity of bending. By adapting and matching a. o. the angle (B) and the bends (8, 10) in the tool, it is possible to compensate away distructive natural oscillations in the tool which, thereby, can be powered and used with high working frequencies without risk of fatigue fractures in the material of the tool.

6 Claims, 2 Drawing Sheets

TOOL FOR CLEANSING TOOTH ROOT CANALS

This application is a continuation-in-part, of application Ser. No. 004,437 filed Dec. 9, 1986, now abandoned.

The present invention relates to a file or broaching tool, in particular for use in cleansing and preparation of tooth root canals and otherwise of the type defined in the opening clause of claim 1. Furthermore, this invention relates to a drive element adapted to drive such a tool and being of the type defined in the opening clause of claim 4.

In connection with root-treatment of a tooth it is important that root canals in the tooth are cleansed effectively. In that connection it is common practice to use a relatively thin round file or broach which is inserted into the root canal and is pulled back and forth therein, while the dentist grasps and manipulates one end or a handle portion of the file with his fingers. For the dentist this is a difficult operation which also may be rather unpleasant for the dentist as well as for the patient, in particular when teeth are to be treated far back in the patient's mouth, since the dentist has to operate with several fingers inserted completely into the patient's mouth in order to use and manipulate the file.

Therefore attempts have been made to mount such a broach or endodontic file at the end of a drive element or drive member of the type which is adapted to be powered by an ultrasonic handpiece of the sorts which are in common use in many dental clinics. Such handpieces include an elongated and relatively slim housing which is used held as a pencil, and the outer end of the housing is adapted for mounting replacable work tools thereon, for instance tools for tooth scaling. The drive member of such work tools is powered to make mechanical and ultrasonic longitudinal vibrations by means of vibratory equipment in the interior of the housing.

Inherently, the ideal pattern of motion for a needle-shaped work tool of the type in question would be a reciprocating movement whereby the tool, or at least its working part, is integrally moved in a generally axial motion. Therefore it would be natural to mount the work tool or needle as a direct extension of the bar-shaped drive stem of the drive member. This would, however, result in that it would be almost impossible to use the needle in the patient's mouth when the ultrasonic handpiece is held and manipulated in the usual manner, i.e. held as a pencil.

Thus, for practical reasons the axis of the needle or its working direction cannot coincide with the principle direction of motion for the powering mechanical vibrations which are generated by the ultrasonic handpiece and are transferred to the needle through the drive instrument for the needle. Consequently, the powering vibrations will provide substantial transversal oscillations in the needle. As a consequence, it has been necessary to use frequencies of movement which are substantially below the resonant frequencies of the needle since, otherwise, these resonant frequencies would be excited and result in transversal natural oscillations in the needle. Typically, such natural oscillations will be undamped and will, consequently, be very unfortunate and straining for the material of the needle which, after a rather short period of use, will break because of fatique fractures in the material. This has been a problem in connection with previous attempts of mounting and powering a root canal file or broach needle by means of a drive instrument and an ultrasonic handpiece of the type mentioned above.

When a needle is operating in a tooth root canal, it would be an advantage—a.o. of less discomfort to the patient—if the amplitude of motion of the needle is as small as possible. However, the amplitude is inversely proportional to the frequency of motion and when a given amount of work is to be made within a specific period of time, then the desire as to a small amplitude will lead to a need of a frequency as high as possible and, again, this would result in risks of fractures in the needle.

In a commercially available instrument of the type in question a straight needle or root canal file is removably mounted as an axial extension of a bar-shaped drive member and in order to achieve an appropriate working position for the needle, the drive member is shaped with a bend which directs the needle in an appropriate direction relative to the main axis of the instrument. However, the bend of the drive member will provide or give rise to substantial transversal oscillations in the needle and, consequently, it is only possible to operate at relatively low frequencies, if needle breakage is to be avoided. Moreover, the manner of mounting the needle makes it necessary to use a particular collect chuck at the end of the drive member in order to avoid that the needle comes loose during use.

Another commercially available instrument of the type under consideration makes use of a straight needle or root canal file which is attached in a particular head portion at the outermost end of a bar-shaped drive member. The head portion is designed as an unsymmetrical body relative to the longitudinal axis or the axis of oscillation of the drive member. As a result of the lacking symmetry this head portion will perform a pattern of oscillation which includes special components of vibration having a main direction which is transverse to the powering longitudinal oscillations in the drive member. The straight needle is attached to the head portion and is directed in the direction of these special components of vibration. However, such a head portion is awkward to use in the patient's mouth and, moreover, inappropriate or destructive transversal oscillations will still be provided in the needle.

On the above background it is an object of this invention to provide a tool of the type introductorily defined which can be powered to operate with high frequencies without the risk of destructive oscillations being excited in the tool.

This is accomplished with the tool of the present invention which is characterized by the features defined in the characterizing clause of claim 1.

Thus, a tool according to the invention can advantageously be used in a drive member of an instrument of the type just mentioned in which the outer or distal end of the drive member is shaped as a head which makes special oscillations with components transverse to the main direction of the powering longitudinal vibrations. However, the best results are obtainable when using the tool of this invention in a drive instrument in accordance with the invention which is characterized by the features defined in the characterizing clause of claim 4. Thus, the angled part of the drive stem and the bending of the tool shank can be matched together in such a manner that unfortunately directed vibration components can be suppressed to a substantial extent.

In the following special aspects and advantages of the invention will be described on the basis of specific embodiments illustrated on the drawing in which.

Figure 1:
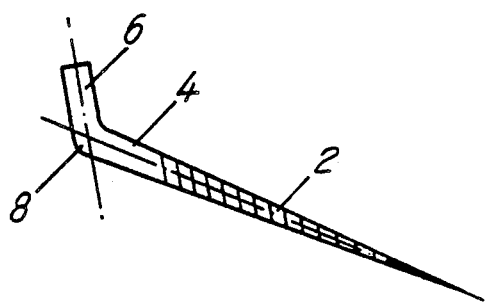
FIG. 1 shows a tool in accordance with the invention as seen from one side.

Referring now to the drawing, FIG. 1 thereof shows a tool according to the invention which includes a generally straight working portion 2 which merges into a shank portion 4. As schematically indicated, the working portion 2 is provided with appropriate cutting edges which may be of the type used on a usual broaching needle or endodontic file. In FIG. 1 the shank portion 4 has a bend 8 so that a shank end 6 is provided and is adapted for attachement in a drive instrument, and an axis of the shank end defines an angle with the axis of the working portion 2.

Figure 2:
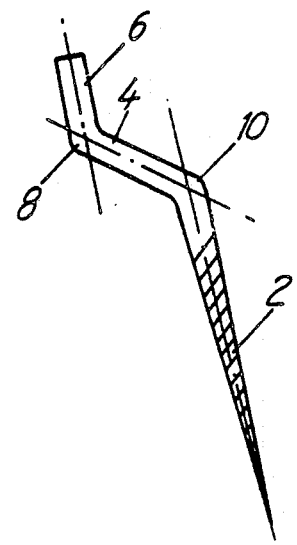
FIG. 2 is a side elevation similar to FIG. 1 but showing a preferred embodiment of the tool of the invention.

FIG. 2 illustrates a preferred embodiment which also has a further bend 10 in its shank portion 4 so that the shank portion includes two oppositely directed bends 8, 10 with parallel axes of bending. The bend 10 which is closest to the working portion 2, may advantageously be more rounded than the first bend 8. The two bends 8, 10 need not be so adapted that the axis of the shank end 6 is parallel with the axis of the working portion 2.

Figure 3:
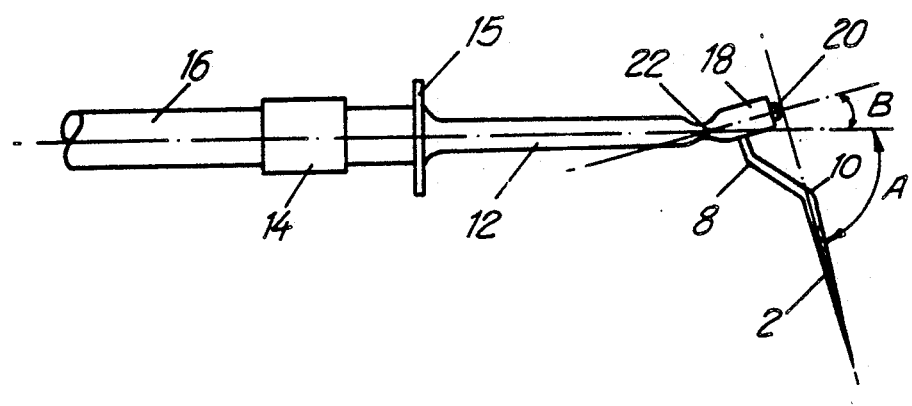
FIG. 3 is a side elevation showing a tool as that of FIG. 2 attached into a preferred embodiment of the drive instrument in accordance with the invention.

Referring now to FIG. 3 a drive instrument according to the invention includes a generally bar-shaped drive member 12 having a proximal end portion 14 adapted for insertion into an ultrasonic handpiece. The proximal end portion 14 includes means for coupling to the oscillator equipment of the handpiece so that longitudinal high frequency vibrations are provided in the drive member 12. In the embodiment shown these coupling means comprise a socket whereby the drive member 12 is rigidly connected with one end of a usual ferrite core indicated at 16. This core is part of the oscillator equipment and high frequency longitudinal vibrations are generated in the core by means of an alternating magnetic field provided in the handpiece.

In the embodiment shown the vibration providing core 16 is permanently connected with the socket on the end portion 14 and, accordingly, the core 16 can be regarded as being a part of the drive member 12. This is expedient but is not an absolute necessity, the main thing being that one end of the drive member 12 is quickly and easily insertable into a handpiece of the type contemplated and during the insertion can be effectively coupled together with the powering or vibratory device of the handpiece so that longitudial vibrations are provided in the drive member 12.

The drive member 12 may also include a flange 15 for use in the mounting in the handpiece. Preferably, the various components of the drive member are also so adapted that the powering longitudinal vibrations in the drive member 12 will include a nodal center at the flange 15 and a maximum of motion close by the other or distal end 18 of the drive member.

Generally considered, the distal end of the drive member 12 is designed as a separate oscillating body with a center of gravity which is offset relative to the longitudinal axis or the axis of vibration for the drive member 12. This particular oscillating body will, accordingly, perform a separate oscillatory pattern about an axis which is indicated at 22, and these oscillations will include substantial components acting transverse to the powering longitudinal vibrations in the drive member 12.

In other words this particular oscillating body at the distal end 18 of the drive member could be regarded as a separate oscillatory system which transforms or redirects a part of the powering longitudinal vibrations in the drive member 12 into oscillations which act generally transverse to the main direction of the powering longitudinal vibrations. These redirected oscillations can be used to power a tool or a needle, and the influences thereon will include a substantially less content of transversal components compared to a corresponding tool which is attached in and powered by an entirely straight drive member with uniform cross section.

Because of the offset center of gravity, the movements at the particular body at the distal end 18 of the drive member will be elliptical in a plane defined by the longitudinal axis of the drive member and an axis which extends through the point 22 and the center of gravity for the body at the end 18. This elliptical movement can be stabilized when the nodal center at the flange 15 is fixed or retained.

If a tool of this invention as that of FIG. 1 or FIG. 2 is considered separately, and if the working portion 2 is supposed to be powered at its free end with a powering longitudinal vibration, then the angled shank end 6 would also be able to transform longitudinal vibrations in a similar manner, since also the shank end 6 has a center of gravity which is offset relative to the longitudinal axis of the working portion 2. In this situation the shank end 6 would, accordingly, also perform an elliptical movement.

By an appropriate shaping the two elliptical patterns of motion can be made to correspond to each other as regards size and shape. Simultaneously, the resonant frequencies of the two elliptical oscillations can be so adapted that they are in the same frequency area, but yet they are so different that one oscillation cannot generate the other one. Typically, this means that the resonant frequencies differ from each other by a factor in the range from 2 to 10.

When the two patterns of motion are coupled together, for instance as shown in FIG. 3, and if the two coupled systems are powered by longitudinal vibrations in the drive member 12, then the resonances in the tool will be removed or suppressed, because the tool is powered in the correct—or almost correct—pattern of motion, but with a mis-matched frequency. Consequently, the body or mass at the distal end 18 will control or drive the tool in the pattern of motion which is determined by the body and can propagate into the entire tool in the shape of oscillations with very small amplitudes, because the oscillations are not in harmony with the geometry and natural oscillations of the tool. Since the amplitudes are small the strains in the tool material are also small, and destructive oscillations are not provided in the tool material.

Accordingly, the tool of this invention can be powered with high frequency and long lifetime by means of a drive instrument of the type described above having a distal end or mass 18 with an offset center of gravity.

The drive instrument according to this invention is particular by having the distal end 18 angled about the axis 22 to angle B relative to the drive member 12, and there is no need of a specially shaped and perhaps bulky head which easily will get in the way during use of the tool in the patient's mouth. However, the length of the end portion 18 should preferably be short—for instance of the same order of magnitude as the diameter of the end portion 18.

In order to tune or match the special oscillatory system of which the end portion 18 is a part, to the powering vibratory system it is expedient to make a local reduction of the dimension of material of the drive member 12 at the area of bending about the axis 22. In the embodiment shown this reduction is made as local flattenings 24, whereby the transverse dimension of the drive member is not reduced—but is rather somewhat increased—in the direction of axis 22, i.e. at right angles to the drawings plane in FIG. 3.

Thereby, the area about the axis 22 will operate as a sort of hinge which has bigger or smaller bending rigidity according to how much the material thickness has been reduced at 24. In this manner the mass or body at the end 18 can be made to oscillate with frequencies which are lower than the generator frequency, and if the difference is sufficiently big, then the generator frequency (from core 16) will be able to maintain the oscillations in the angled drive member end 18.

Thus, there is provided a system or an equipment, whereby powering ultrasonic vibrations (as an example 42 Kh can be transmitted to and power a tool at a lower frequency) which still is very high compared to previously obtained or obtainable working frequencies in tools of the type in question. Simultaneously, compensations have been made for the tendency of the tool to perform destructive natural oscillations.

Moreover, the angled end portion 18 and the angled shank portion of the tool in accordance with the invention can be used to obtain that the working portion 2 of the tool attains an appropriate angle A relative to the longitudinal direction of the drive member 12 and of the entire handpiece.

Figure 4:
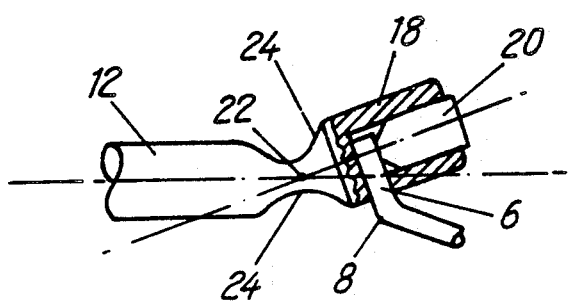
FIG. 4 is a side elevation showing—partially in section and enlarged—the distal end of the drive instrument of FIG. 3.

As shown in FIG. 4 the clamping of the shank end 6 of the tool in the distal end 18 of the drive member can appropriately be accomplished by means of a transverse bore which possibly may be through-going, in the end portion 18, and an appropriately recessed screw may be used to safely secure the tool in place, as indicated at 20 in FIG. 4.

The first bend 8 of the tool shank 4 should preferably be rather close to the surface of the end portion 18, when the tool is mounted and secured therein. In addition the tool should be secured in such a position that the bending axis 22 in the drive member 12 is parallel with each bending axis in the tool of the invention.

Figure 5:
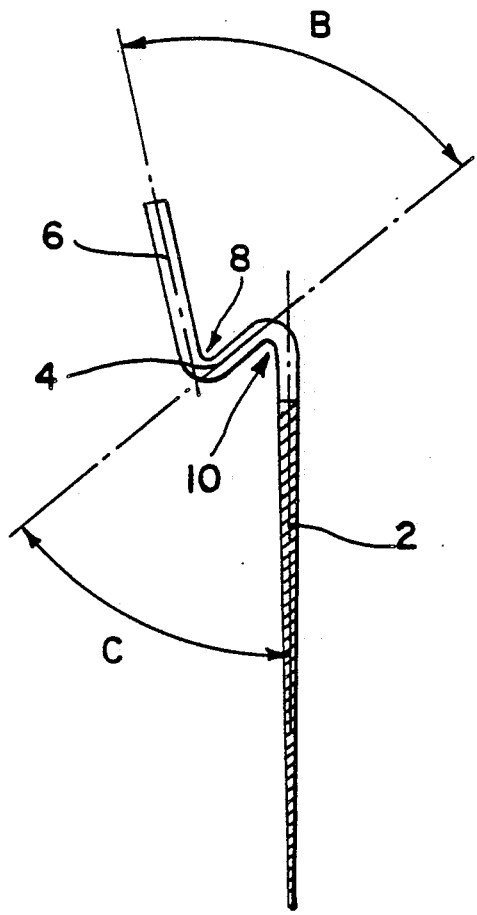
FIGS. 5 and 6 show respective further embodiments of the tool.
Figure 6:
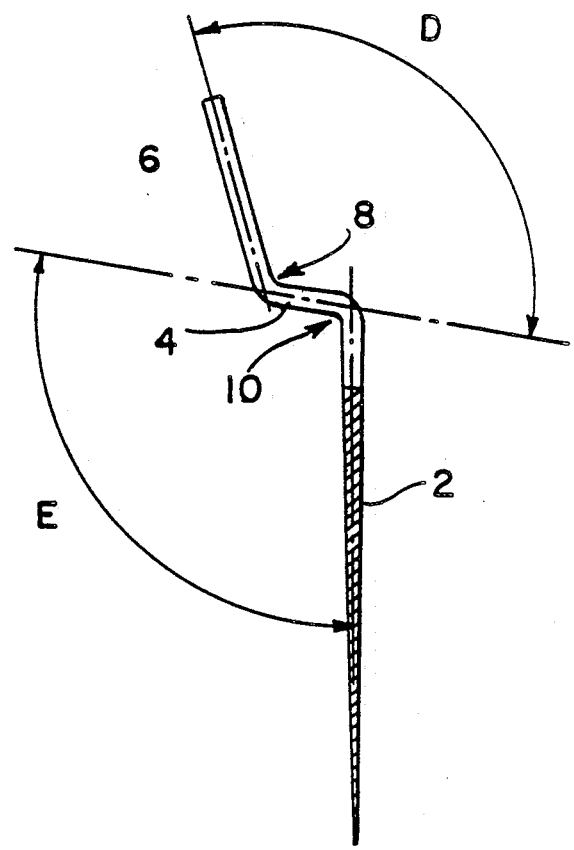

FIGS. 5 and 6 illustrate respective further embodiments of the endodontic tool or file of the present invention. As in FIG. 2 each of these further embodiments has a shank portion 4 including a double bend which comprises a first bend 8 and a second bend 10 directed oppositely to the first bend. The axis of bending of the first bend 8 is parallel to that of the second bend 10.

The respective angles of bending depend on several factors, in particular on the diameter of the file. Moreover, the angles of bending depend on the length of the working portion 2 and on the material of which the file has been made.

The embodiment of FIG. 5 has a type of double bend which has proven to be very efficient for thinner files with a shank diameter in the order of 0.5 mm. As shown, the first bend 8 defines an acute angle B, while the second bend 10 defines an actue angle C.

The embodiment of FIG. 6 has another type of double bend which has proven to be very efficient for thicker files with a shank diameter in the order of 0.6 to 0.8 mm. In this embodiment the first bend 8 and the second bend 10 define respective obtuse angles D and E.

For the purpose of further illustration and understanding reference is made to the following examples of dimensions.

While the tool and drive instrument of this invention primarily have been developed for use in connection with root treatments of teeth, the tool of the invention has turned out to be so efficient that it is very suitable as a proper drilling tool, for instance for making very fine holes in bone tissues or other materials with similar character and hardness. A contributing reason of this is that relatively big amounts of energy (as an example 5 watts) can be transferred with equipment in accordance with the invention.

I claim:

1. An endodontic tool for directing ultrasonic vibrations in connection with cleansing and preparation of tooth root canals; said tool comprising a generally straight and needle-shaped working portion and a shank portion for mounting and firmly securing in a drive instrument of the type adapted to be operatively coupled to an ultrasonic vibratory handpiece, characterized by said shank portion including two oppositely directed bends with parallel axes of bending, said bends being selected to provide a configuration for transforming and directing ultrasonic vibrations from said handpiece and drive instrument into the direction of a longitudinal axis of said generally straight working portion.

2. An endodontic tool in accordance with claim 1, further comprising a drive instrument comprising a generally bar-shaped drive member having a proximal end portion which is adapted to be operatively coupled to an ultrasonic vibratory handpiece in order to be powered thereby to make longitudinal mechanical vibrations, and a distal end portion which is adapted and shaped as a head portion with means for removably mounting and firmly clamping a shank end of said endodontic tool, said head portion being designed to perform a particular pattern of oscillations including components of oscillation with a main direction which is transverse to said longitudinal vibrations, characterized by said head portion being defined by an angled distal end portion of said generally bar-shaped drive member, the angle of said distal end portion being matched to said bends of said shank portion in order to compensate away resonances in the tool.

3. A drive instrument in accordance with claim 1, characterized in that said generally bar-shaped drive member has a local reduction of thickness at the area of bending thereof.

4. An endodontic tool in accordance with claim 1, characterized by each of said two oppositely directed bends defining acute angle.

5. An endodontic tool in accordance with claim 1, characterized by each of said two oppositely directed bends defining an obtuse angle.

6. In combination, a drive instrument comprising a generally bar-shaped drive member having a proximal end portion adapted to be operatively coupled to an ultrasonic vibratory handpiece in order to be powered thereby to make longitudinal mechanical vibrations and having a head portion defined by an angled distal end portion of said generally bar-shaped drive member, said head portion performing a predetermined pattern of oscillations, including components of oscillation with a main direction transverse to said longitudinal vibrations, when said instrument is in operation, and an endodontic tool having a shank portion mounted upon and firmly secured to said head portion and a straight, needle-shaped working portion, said shank portion including two oppositely-directed bends with parallel axes of bending, said bends being selected to provide a configuration for transferring and directing ultrasonic vibrations from said drive instrument into the direction of a longitudinal axis of said straight working portion.

* * * * *